US008540728B2

(12) United States Patent
Woehr et al.

(10) Patent No.: US 8,540,728 B2
(45) Date of Patent: *Sep. 24, 2013

(54) CATHETER INSERTION DEVICE

(71) Applicant: B. Braun Melsungen AG, Melsungen (DE)

(72) Inventors: Kevin Woehr, Felsberg (DE); Kenneth C. Raines, Bethlehem, PA (US)

(73) Assignee: B. Braun Melsungen AG, Melsungen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/630,251

(22) Filed: Sep. 28, 2012

(65) Prior Publication Data

US 2013/0046315 A1 Feb. 21, 2013

Related U.S. Application Data

(63) Continuation of application No. 13/425,140, filed on Mar. 20, 2012, now Pat. No. 8,337,463, which is a continuation of application No. 12/790,630, filed on May 28, 2010, now Pat. No. 8,328,762, which is a continuation of application No. 10/520,325, filed as application No. PCT/EP03/07073 on Jul. 2, 2003, now Pat. No. 7,736,339.

(30) Foreign Application Priority Data

Jul. 4, 2002 (DE) .............................. 202 10 394 U

(51) Int. Cl.
A61M 25/01 (2006.01)
A61B 17/34 (2006.01)

(52) U.S. Cl.
USPC ...................................... 606/108; 604/164.08

(58) Field of Classification Search
USPC .......... 606/108; 604/164.01, 164.08, 165.01, 604/164.02; 29/428, 592
See application file for complete search history.

(56) References Cited

U.S. PATENT DOCUMENTS 3,601,151 A 8/1971 Winnard
4,143,853 A * 3/1979 Abramson ................. 251/149.1
(Continued)

FOREIGN PATENT DOCUMENTS

AU 2003246358 B2 1/2004
DE 30 00 903 A1 1/1980
(Continued)

OTHER PUBLICATIONS

Statutory Declaration of Kevin Woehr, Executed on Sep. 15, 2011, In the matter of Australian Patent Application No. 2003246358 and in the matter of Opposition thereto by Terumo Corporation, including Exhibits KW-1 to KW-7 (101 pages).

(Continued)

Primary Examiner — Kevin C Sirmons
Assistant Examiner — Michael J Anderson
(74) Attorney, Agent, or Firm — Klein, O'Neill & Singh, LLP

(57) ABSTRACT

Embodiments of a catheter insertion device are discussed comprising: an approximately hollow cylindrical catheter sleeve, at whose distal end a catheter is attached: a needle sleeve with a hollow needle, which is attached thereto and which, when ready for use, extends through the catheter sleeve and the catheter, and; a needle protective element that is arranged inside the catheter sleeve while being able to move on the needle. Said needle protective element has an engaging section that engages with an engaging device, which is formed in the vicinity of the needle tip, when the hollow needle is withdrawn from the catheter sleeve. A check valve is placed inside the catheter sleeve between the catheter and the needle protective element. The hollow needle, when ready for use, extends through said check valve, and the check valve automatically closes once the needle is withdrawn.

29 Claims, 3 Drawing Sheets

(56) References Cited

U.S. PATENT DOCUMENTS

Figure 1:
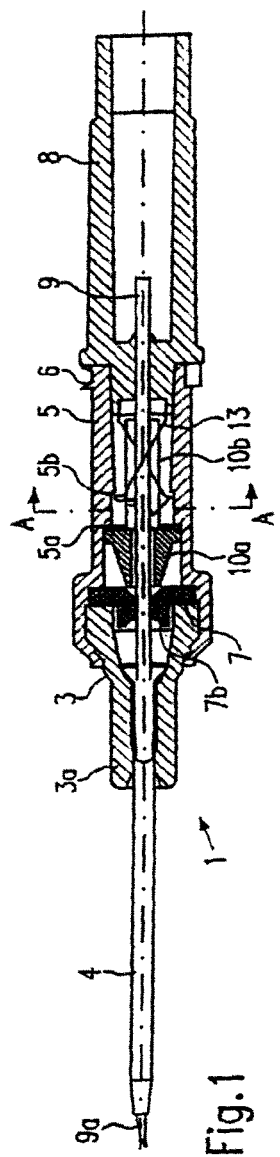

| Patent No. | | Date | Inventor | Class |
|---|---|---|---|---|
| 4,387,879 A | | 6/1983 | Tauschinski | |
| 4,449,693 A | | 5/1984 | Gereg | |
| 4,511,359 A | | 4/1985 | Vaillancourt | |
| 4,512,766 A | * | 4/1985 | Vailancourt | 604/167.03 |
| 4,578,063 A | | 3/1986 | Inman et al. | |
| 4,673,399 A | | 6/1987 | Pruett | |
| 4,765,588 A | | 8/1988 | Atkinson | |
| 4,772,266 A | | 9/1988 | Groshong | |
| 4,795,432 A | | 1/1989 | Karczmer | |
| 4,813,938 A | | 3/1989 | Raulerson | |
| 4,842,591 A | * | 6/1989 | Luther | 604/537 |
| 4,846,809 A | | 7/1989 | Sims | |
| 4,874,377 A | | 10/1989 | Newgard et al. | |
| 4,883,461 A | | 11/1989 | Sawyer | |
| 4,917,668 A | * | 4/1990 | Haindl | 604/167.03 |
| 4,927,414 A | | 5/1990 | Kulli | |
| 4,929,235 A | | 5/1990 | Merry et al. | |
| 4,929,241 A | | 5/1990 | Kulli | |
| 4,944,725 A | | 7/1990 | McDonald | |
| 4,944,728 A | * | 7/1990 | Carrell et al. | 604/164.08 |
| 4,952,207 A | * | 8/1990 | Lemieux | 604/164.08 |
| 4,964,854 A | | 10/1990 | Luther | |
| 4,966,586 A | | 10/1990 | Vaillancourt | |
| 4,978,344 A | | 12/1990 | Dombrowski et al. | |
| 5,051,109 A | | 9/1991 | Simon | |
| 5,053,014 A | | 10/1991 | Van Heugten | |
| 5,053,017 A | | 10/1991 | Chamuel | |
| 5,062,836 A | | 11/1991 | Wendell | |
| 5,084,023 A | | 1/1992 | Lemieux | |
| 5,108,374 A | | 4/1992 | Lemieux | |
| 5,127,905 A | | 7/1992 | Lemieux | |
| 5,135,504 A | | 8/1992 | McLees | |
| 5,147,327 A | | 9/1992 | Johnson | |
| 5,154,703 A | | 10/1992 | Bonaldo | |
| 5,156,596 A | | 10/1992 | Balbierz et al. | |
| 5,158,554 A | | 10/1992 | Jepson et al. | |
| 5,180,370 A | | 1/1993 | Gillespie | |
| 5,188,607 A | | 2/1993 | Wu | |
| 5,195,980 A | | 3/1993 | Catlin | |
| 5,215,528 A | | 6/1993 | Purdy et al. | |
| 5,234,410 A | | 8/1993 | Graham et al. | |
| 5,242,393 A | | 9/1993 | Brimhall et al. | |
| RE34,416 E | | 10/1993 | Lemieux | |
| 5,269,771 A | | 12/1993 | Thomas et al. | |
| 5,300,033 A | | 4/1994 | Miller | |
| 5,312,355 A | | 5/1994 | Lee | |
| 5,322,517 A | * | 6/1994 | Sircom et al. | 604/198 |
| 5,328,482 A | | 7/1994 | Sircom et al. | |
| 5,334,158 A | | 8/1994 | McLees | |
| 5,334,159 A | | 8/1994 | Turkel | |
| 5,344,408 A | | 9/1994 | Partika | |
| 5,352,205 A | | 10/1994 | Dales et al. | |
| 5,380,305 A | | 1/1995 | Ghouri | |
| 5,405,323 A | | 4/1995 | Rogers et al. | |
| 5,409,461 A | | 4/1995 | Steinman | |
| 5,419,766 A | | 5/1995 | Chang et al. | |
| 5,454,790 A | | 10/1995 | Dubrul | |
| 5,456,675 A | | 10/1995 | Wolbring et al. | |
| 5,458,640 A | | 10/1995 | Gerrone | |
| 5,458,658 A | | 10/1995 | Sircom | |
| 5,558,651 A | | 9/1996 | Crawford et al. | |
| 5,562,633 A | | 10/1996 | Nichols | |
| 5,562,633 A | | 10/1996 | Wozencroft | |
| 5,584,809 A | | 12/1996 | Gaba | |
| 5,601,536 A | | 2/1997 | Crawford et al. | |
| 5,613,663 A | | 3/1997 | Schmidt et al. | |
| 5,634,913 A | * | 6/1997 | Stinger | 604/272 |
| 5,651,772 A | | 7/1997 | Arnett | |
| 5,662,610 A | | 9/1997 | Sircom | |
| 5,688,253 A | | 11/1997 | Paradis | |
| 5,718,688 A | | 2/1998 | Wozencroft | |
| 5,725,503 A | | 3/1998 | Arnett | |
| 5,738,144 A | | 4/1998 | Rogers | |
| 5,749,857 A | | 5/1998 | Cuppy | |
| 5,779,681 A | | 7/1998 | Bonn | |
| D397,434 S | | 8/1998 | Pike | |
| 5,817,069 A | | 10/1998 | Arnett | |
| 5,830,189 A | | 11/1998 | Chang | |
| 5,851,196 A | | 12/1998 | Arnett | |
| 5,865,806 A | | 2/1999 | Howell | |
| 5,879,337 A | | 3/1999 | Kuracina et al. | |
| 5,911,705 A | | 6/1999 | Howell | |
| 5,911,710 A | | 6/1999 | Barry et al. | |
| 5,935,104 A | | 8/1999 | Janek et al. | |
| 5,954,698 A | | 9/1999 | Pike | |
| 5,967,490 A | | 10/1999 | Pike | |
| 5,971,957 A | | 10/1999 | Luther et al. | |
| 6,001,080 A | | 12/1999 | Kuracina et al. | |
| 6,004,294 A | | 12/1999 | Brimhall et al. | |
| 6,077,244 A | | 6/2000 | Botich et al. | |
| 6,080,137 A | | 6/2000 | Pike | |
| 6,117,108 A | * | 9/2000 | Woehr et al. | 604/110 |
| 6,171,287 B1 | | 1/2001 | Lynn et al. | |
| 6,203,527 B1 | * | 3/2001 | Zadini et al. | 604/110 |
| 6,228,060 B1 | | 5/2001 | Howell | |
| 6,287,278 B1 | * | 9/2001 | Woehr et al. | 604/110 |
| 6,322,537 B1 | * | 11/2001 | Chang | 604/164.08 |
| 6,352,520 B1 | | 3/2002 | Miyazaki | |
| 6,379,333 B1 | | 4/2002 | Brimhall et al. | |
| 6,379,372 B1 | | 4/2002 | Dehdashtian et al. | |
| 6,443,927 B1 | | 9/2002 | Cook | |
| 6,443,929 B1 | | 9/2002 | Kuracina et al. | |
| 6,485,468 B2 | | 11/2002 | Vojtasek | |
| 6,506,181 B2 | | 1/2003 | Meng et al. | |
| 6,533,759 B1 | | 3/2003 | Watson et al. | |
| 6,585,704 B2 | * | 7/2003 | Luther et al. | 604/263 |
| 6,595,954 B1 | | 7/2003 | Luther et al. | |
| 6,595,955 B2 | | 7/2003 | Ferguson et al. | |
| 6,616,630 B1 | * | 9/2003 | Woehr et al. | 604/110 |
| 6,629,959 B2 | | 10/2003 | Kuracina et al. | |
| 6,652,486 B2 | * | 11/2003 | Bialecki et al. | 604/110 |
| 6,652,490 B2 | | 11/2003 | Howell | |
| 6,689,102 B2 | * | 2/2004 | Greene | 604/164.08 |
| 6,692,471 B2 | | 2/2004 | Boudreaux | |
| 6,695,814 B2 | * | 2/2004 | Greene et al. | 604/164.08 |
| 6,699,221 B2 | | 3/2004 | Vaillancourt | |
| 6,709,419 B2 | | 3/2004 | Woehr | |
| 6,719,726 B2 | | 4/2004 | Meng et al. | |
| 6,749,588 B1 | | 6/2004 | Howell et al. | |
| 6,764,468 B1 | | 7/2004 | East | |
| 6,860,871 B2 | | 3/2005 | Kuracina et al. | |
| 6,883,778 B1 | | 4/2005 | Newton et al. | |
| 6,902,546 B2 | | 6/2005 | Ferguson | |
| 6,916,311 B2 | | 7/2005 | Vojtasek | |
| 6,958,055 B2 | | 10/2005 | Donnan et al. | |
| 6,972,002 B2 | | 12/2005 | Thorne | |
| 7,008,404 B2 | | 3/2006 | Nakajima | |
| 7,125,396 B2 | | 10/2006 | Leinsing et al. | |
| 7,374,554 B2 | | 5/2008 | Menzi et al. | |
| 7,524,306 B2 | * | 4/2009 | Botich et al. | 604/164.07 |
| 7,635,352 B2 | * | 12/2009 | Adams | 604/164.08 |
| 7,736,339 B2 | * | 6/2010 | Woehr et al. | 604/164.08 |
| 8,333,735 B2 | * | 12/2012 | Woehr et al. | 604/164.08 |
| 8,337,463 B2 | * | 12/2012 | Woehr et al. | 604/164.08 |
| 2002/0128604 A1 | | 9/2002 | Nakajima | |
| 2002/0128605 A1 | | 9/2002 | Miller et al. | |
| 2004/0044313 A1 | | 3/2004 | Nakajima | |
| 2004/0225260 A1 | * | 11/2004 | Villa et al. | 604/164.01 |

FOREIGN PATENT DOCUMENTS

| | | |
|---|---|---|
| DE | 31 00 622 A1 | 4/1980 |
| DE | 32 10 148 A1 | 9/1983 |
| DE | 44 34 569 A1 | 3/1995 |
| DE | 201 04 539 U1 | 1/2002 |
| EP | 0 414 997 A1 | 4/1990 |
| EP | 0 554 841 A1 | 8/1993 |
| EP | 0 747 084 A2 | 12/1996 |
| EP | 0 799 626 A1 | 10/1997 |
| EP | 1 101 508 A2 | 5/2001 |
| EP | 1 101 508 A3 | 8/2001 |
| EP | 1 180 381 A1 | 2/2002 |
| EP | 1 240 916 B1 | 9/2002 |
| EP | 1 374 942 A1 | 1/2004 |
| EP | 1 374 942 B1 | 1/2004 |

| | | |
|---|---|---|
| GB | 2 118 440 A | 11/1983 |
| WO | WO 97/45151 | 12/1997 |
| WO | WO 98/53875 | 12/1998 |
| WO | WO 99/26682 | 6/1999 |
| WO | WO 2004/004819 A1 | 1/2004 |

OTHER PUBLICATIONS

Statutory Declaration of William Samuel Hunter, Executed and Notarized on May 11, 2010, In the matter of Australian Patent Application No. 2003246358 and in the matter of Opposition thereto by Terumo Corporation (43 pages).

Statutory Declaration of Noel J. Akers, Executed and Notarized on Aug. 17, 2011, In the matter of Australian Patent Application No. 2003246358, including Exhibit NJA-1 (48 pages).

Annex 1: Facts and Arguments to the Notice of Opposition to a European Patent; Opponent Smith Medical ASD Inc.; Patentee B. Braun Melsungen AG for Opposed Patent No. EP 1 545 681 B1; dated Oct. 21, 2008 (133 pages).

Appeal and the Grounds for Appeal Filed by Patent Proprietor Against the Decision of the Opposition Division; Opponent Smith Medical ASD Inc.; Patentee B. Braun Melsungen AG for Opposed Patent No. EP 1 545 681 B1; dated Jan. 27, 2011 (77 pages).

Response to Appeal and the Grounds for Appeal Filed by Patent Proprietor Against the Decision of the Opposition Division; Opponent Smith Medical ASD Inc.; Patentee B. Braun Melsungen AG for Opposed Patent No. EP 1 545 681 B1; dated Oct. 21, 2011 (86 pages).

Patent Abstracts of Japan; entitled "Indwelling Puncture Needle With Wing Having Branching Part", Application No. 11-021665, Publication No. 2000-217925; Published Aug. 8, 2000, Applicant Hanako Medical KK (3 pages).

Patent Abstracts of Japan; entitled "Safe Indwelling Needle", Application No. 2000-078335, Publication No. 2001-259029, Published Sep. 25, 2001, Applicant Medikit KK (7 pages).

Patent Abstracts of Japan; entitled "Safety Indwelling Needle", Application No. 2000-182911, Publication No: 2002-000727, Published Jan. 8, 2002, Applicant Medikit KK (4 pages).

Patent Abstracts of Japan; entitled "Indwelling Needle Structure", Application No. 2001-363865, Publication No. 2003-175112, Published Jun. 24, 2003, Applicant Mitsubishi Pencil Co LTD (5 pages).

Patent Abstracts of Japan; entitled "Indwelling Needle Structure and Seal Material Used Therefore", Application No. 2005-035112, Publication No. 2005-261938 A, Published Sep. 29, 2005, Applicant JMS Co LTD (5 pages).

Patent Abstracts of Japan; entitled "Indwelling Needle", Application No. 2004-143931, Publication No. 2005-323762, Published Nov. 24, 2005, Applicant Medikit KK (4 pages).

Patent Abstracts of Japan; entitled "Indwelling Needle", Application No. 1996-0040652, Publication No. 9206375, Published Aug. 12, 1997, Applicant: Togo Medikit KK (2 pages).

"Conical Fittings With 6% (Luer) Taper for Syringes, Needles for Certain Other Medical Equipment—Part 2: Lock fittings," International Standar, ISO 594-2, second edition, 1998, pp. 1-11, Technical Committee ISO/TC 84, Switzerland.

Office Action mailed May 29, 2007 from corresponding U.S. Appl. No. 10/520,325, filed Sep. 12, 2005.

Final Office Action mailed Nov. 14, 2007 from corresponding U.S. Appl. No. 10/520,325, filed Sep. 12, 2005.

Office Action mailed Sep. 26, 2008 from corresponding U.S. Appl. No. 10/520,325, filed Sep. 12, 2005.

Final Office Action mailed Mar. 30, 2009 from corresponding U.S. Appl. No. 10/520,325, filed Sep. 12, 2005.

Final Office Action mailed Jan. 19, 2010 from corresponding U.S. Appl. No. 10/520,325, filed Sep. 12, 2005.

Notice of Allowance mailed Feb. 25, 2010 from corresponding U.S. Appl. No. 10/520,325, filed Sep. 12, 2005.

* cited by examiner

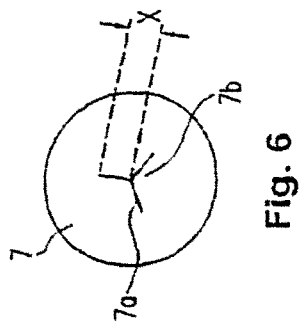
Fig. 6
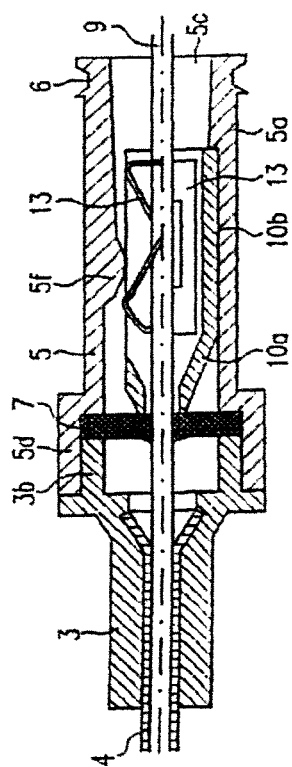
Fig. 5
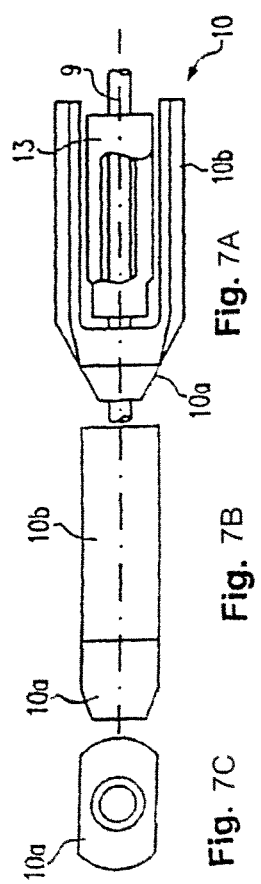
Fig. 7A
Fig. 7B
Fig. 7C
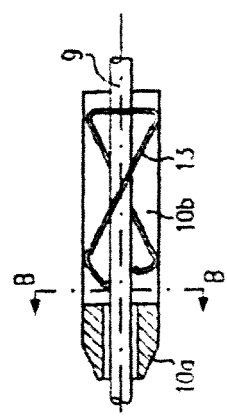
Fig. 7D
Fig. 7E

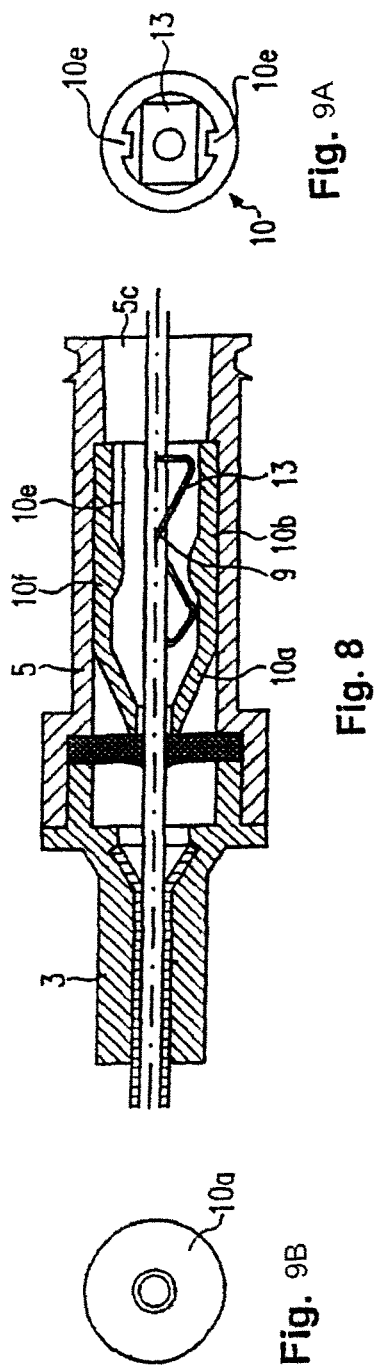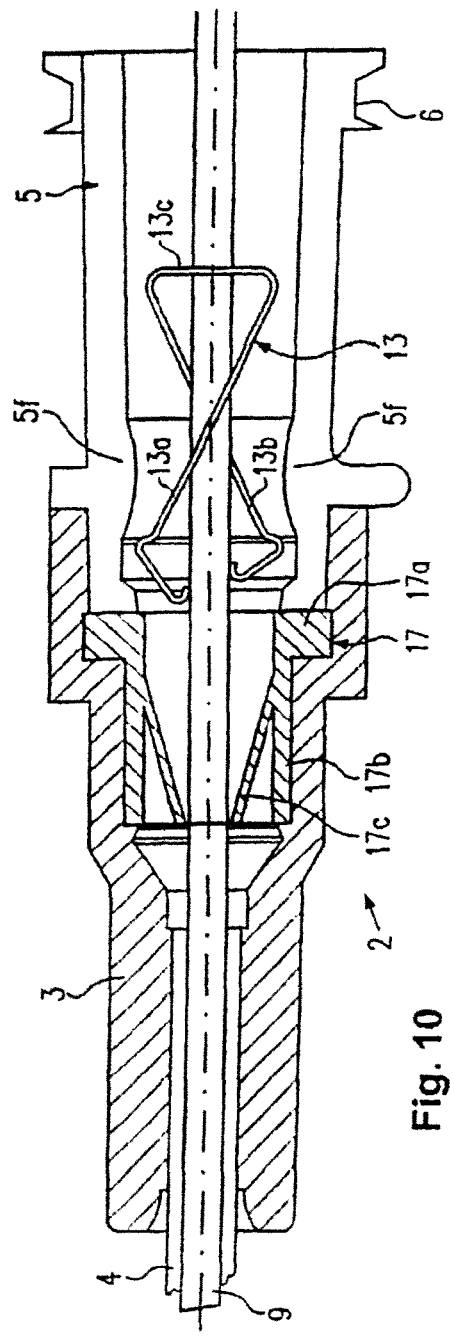

Figure 2:
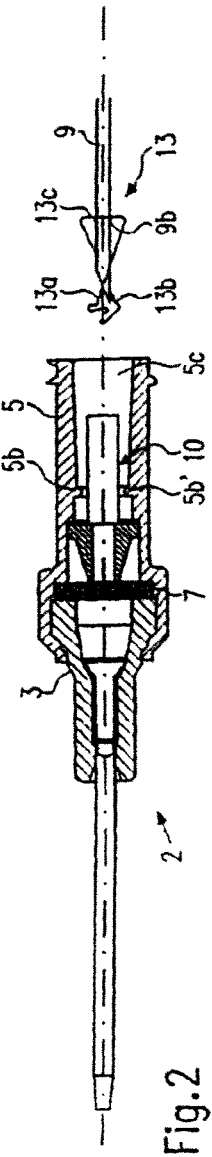

CATHETER INSERTION DEVICE

CROSS-REFERENCE TO RELATED APPLICATIONS

This is a continuation of application Ser. No. 13/425,140, filed Mar. 20, 2012, which is a continuation application of Ser. No. 12/790,630, filed May 28, 2010, which is continuation application of Ser. No. 10/520,325, filed Sep. 12, 2005, which is a national phase application of PCT No. PCT/EP03/07073; the contents of each of the foregoing are expressly incorporated herein by reference.

FIELD

Device, system, and method for a catheter insertion device are generally discussed herein with specific reference to catheter device having a valve opener and a valve.

BACKGROUND

A device of this kind is known from EP 352 928, wherein in a hollow catheter hub a needle guard element is arranged. On withdrawal of the hollow needle from the catheter over an engaging means near the tip of the hollow needle, the needle guard element engages with the engaging means and covers the tip when the hollow needle is separated from the catheter. In this design, after withdrawal of the hollow needle from the catheter, through this catheter blood can issue with which the operating personnel can come into contact.

The invention is based on the object of designing a catheter insertion device of the type described above such that an outflow of blood from the catheter is prevented after removal of the hollow needle with the needle guard element.

SUMMARY

This object is solved according to the invention by the features in the characterizing part of claim 1. In the ready position, a check valve is arranged in the catheter hub between the catheter and the needle guard element. Through this valve the hollow needle extends, so that after withdrawal of the hollow needle from the catheter the latter can be reliably closed such that an outflow of blood is prevented, while simultaneously the tip of the hollow needle is securely covered by the needle guard element so that the operating personnel cannot injure themselves on the needle tip.

BRIEF DESCRIPTION OF THE DRAWINGS

Exemplary embodiments of the invention are explained in more detail below with reference to the drawing, in which:

FIG. 1 shows a longitudinal section through a catheter insertion device in the ready position, FIG. 2 shows the catheter insertion device with the hollow needle removed, FIG. 3 shows the device with an attached syringe, FIG. 4 shows a sectional view along the line A-A in FIG. 1, FIG. 5 shows a longitudinal section through another embodiment, FIG. 6 shows a view of the valve disc, FIGS. 7A, 7B, 7C, 7D, and 7E show different views of a valve actuating element, FIG. 8 shows a longitudinal section through a further embodiment, FIGS. 9A and 9B show front views of the valve actuating element of FIG. 8, and FIG. 10 shows a longitudinal section through a further embodiment.

DETAILED DESCRIPTION

FIG. 1 shows a catheter insertion device 1 having a catheter hub 2 which has a two-part form in the embodiment. A distal hub element 3 of the catheter hub has a holding section 3*a* in which a catheter 4 is press-fitted. The proximal end of the hub element 3 has an enlarged diameter with regard to the distal end and forms a connecting section with a hub element 5 whose distal end overlaps the proximal end of the hub element 3 and which is provided at its proximal end with a Luer thread 6. Between the two hub elements 3 and 5, a check valve in the form of a valve disc 7 is inserted and is fixed in place by the two hub elements 3 and 5.

In the ready position according to FIG. 1, there is inserted in the catheter hub 2 a needle hub 8 to which a hollow needle 9 is fixed which extends through the valve disc 7 and the catheter 4 so that the needle tip 9*a* is exposed. Between needle hub 8 and valve disc 7 there is displaceably arranged in the proximal hub element 5 a valve actuating element 10 which has a truncated cone-shaped locating section 10*a* which serves to open the valve disc 7, as FIG. 3 shows. On the proximal side, a plunger section 10*b* adjoins the locating section 10*a* and has a hollow space for receiving a needle guard element 13. In the embodiment shown, the plunger section 10*b* is formed by two spaced plungers between which the needle guard element in the form of a spring clip 13 is inserted, as shown in the cross-sectional view in FIG. 4.

On withdrawal of the hollow needle 9 from the catheter hub 2, an engaging means 9*b* (FIG. 2), provided near the needle tip 9*a* and having the form of a radial projection on the hollow needle which can be formed by light crimping, engages with the outer circumference of a bore in the rear wall 13*c* of the spring clip 13, so that the spring clip 13 is removed from the catheter hub with the needle 9, while simultaneously the spring arms 13*a* and 13*b* of the spring clip cover the needle tip, completely protecting and blocking it. In this separated position shown in FIG. 2, the valve disc 7, due to its elasticity, closes the through-hole for the hollow needle 9 so that no blood can flow out through the catheter 4. As FIG. 6 shows, the valve disc is provided for example with three slits 7*a* starting from the middle and extending radially over a short section X, forming elastic flaps 7*b* therebetween which can be expanded by the hollow needle.

FIG. 3 shows the insertion of a syringe 14 in the catheter hub 2, wherein the neck portion 14*a* of the syringe comes to abut on the plunger section 10*b* of the valve actuating element 10 and presses it against the valve disc 7, so that the truncated cone-shaped locating section 10*a* outwardly displaces the flaps 7*b* of the valve disc and thereby opens the valve, so that a liquid can be inserted from the syringe 14 into the catheter 4.

The incline of the truncated cone on the locating section 10*a* and the displacement path of the actuating element 10 relative to the valve disc 7 are designed such that due to the elasticity of the material of the valve disc 7, the flaps 7*b* displace the locating section 10*a* to the right in FIG. 3 when the syringe 14 is removed from the catheter hub 2. Hereby, the valve disc 7 is automatically closed, as the position in FIG. 2 shows.

In the hub element 5, there is formed by a shoulder 5*a* a stop for the actuating element 10, to define the position of the actuating element in the separated position in FIG. 2. Hereby, the truncated cone-shaped locating section 10*a* lies near the stop 5*a*, while its distal end abuts on the valve disc 7 as shown in FIG. 2. The radial slits 7a of the valve disc 7 are designed such that in the ready position in FIG. 1, the flaps 7b are bent radially upwards less than in the open position by the locating section 10a in FIG. 3.

Figure 4:
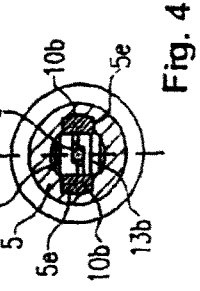

As the cross-sectional view in FIG. 4 shows, the two plungers lob of the valve actuating element 10 are guided in longitudinal grooves 5e of the hub element 5 and they project radially inwards into the bore 5c of the hub element 5, so that they form an abutting surface for the neck portion 14a of the syringe 14. The bore 5c in the hub element 5 is formed slightly conically corresponding to the conical neck portion 14a of a syringe.

On the inner circumference of the bore 5c of the hub element 5, a further shoulder 5b having a smaller diameter is formed, on which the radially outer areas of the spring arms 13a and 13b abut in the ready position in FIG. 1. Hereby, the spring clip 13 is fixed in its position in the hub element 5. When the needle hub 8 with the hollow needle 9 is removed from the catheter hub 2, first the spring clip 13 is held on the shoulder 5b by abutting until the radial projection 9b comes to abut on the rear wall 13c of the spring clip. In this position, the two spring arms 13a, 13b can be released from the shoulder 5b and spring back inwards to cover the needle tip, as FIG. 2 shows, whereupon the spring clip 13 with the hollow needle 9 can be removed from the catheter hub.

Figure 3:
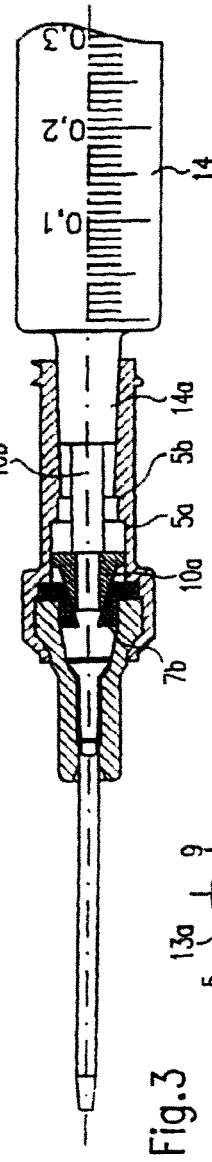

In the embodiment according to FIGS. 1 to 3, the distal end section of the hub element 5 is shrunk, welded or bonded onto the proximal end section of the hub element 3 after the valve actuating element 10 and the valve disc 7 are inserted in the hub element 5. It is also possible to join the two hub elements 3 and 5 to one another, for example by a thread which is secured against loosening after assembly. The spring clip 13 is inserted together with the hollow needle 9 in the bore 5c of the hub element 5 during assembly, wherein the radially outer areas of the spring arms 13a, 13b snap in at the shoulder 5b under elastic deformation.

Preferably, in front of the shoulder 5b a projection 5b' can be formed in the bore 5c of the hub element, as shown in FIG. 2. Hereby the snap-in and holding effect of the spring clip 13 is increased.

FIG. 5 shows a modified embodiment of the connection of the two hub elements 3 and 5, in which two cylindrical sections 3b and 5d engage in one another. A thread can be provided between these two cylindrical sections. However, it is also possible to bond or weld these two sections.

In this embodiment, the valve actuating element 10 is also modified in relation to the embodiment of FIGS. 1 to 3. FIG. 7A shows a side view of the approximately U-shaped actuating element 10 with the spring clip 13 inserted therein. As the side view rotated by 90.degree. in FIG. 7B shows, the locating section 10a is partly flattened on opposite sides so that the width of the plunger sections 10b extends into the locating section 10a. FIG. 7C is a front view from the left in FIG. 7B and shows the flattened structure of the locating section 10a. FIG. 7D is a sectional view along the central line in FIG. 7B. FIG. 7E shows a section through the valve actuating element 10 along the line B-B in FIG. 7D.

FIG. 5 shows the lower half of the valve actuating element 10 corresponding to the view in FIG. 7A, and the upper half in a sectional view rotated by 90.degree. corresponding to FIG. 7B. The shoulder 5a for positioning the valve actuating element 10 in the hub element 5 is hereby formed on the ends of the diametrically opposite grooves 5e (FIG. 4), so that the proximal ends of the plunger sections 10b abut on the shoulders 5a. Corresponding to the shoulder 5b in FIGS. 1 to 3 in the embodiment in FIG. 5, there is formed on the hub element 5 a projection 5f which projects inwards at diametrically opposite positions on the bore 5c of the hub element 5 and fixes the spring clip 13 in the hub element 5 until the spring arms 13a, 13b spring inwards over the needle tip and the spring clip with the hollow needle 9 is removed from the catheter hub.

FIG. 8 shows a modified embodiment having a hollow cylindrical valve actuating element 10 on whose inner circumference a projection 10f is formed for positioning the spring clip 13 inside the valve actuating element 10. FIG. 9A shows a front view of the valve actuating element 10 from the right and FIG. 9B shows a front view from the left in FIG. 8, wherein for locating the neck portion 14a of a syringe 14, in this embodiment radially inwardly projecting ribs 10e are formed which protrude radially into the bore 5c of the hub element 5, as the upper half of the valve actuating element in FIG. 8 shows, in which the sectional view of the lower half of the valve actuating element 10 is shown rotated by 90.degree. in relation to the upper half.

FIG. 10 shows a modified embodiment wherein between the two hub elements 3 and 5 a check valve 17 is inserted, which has a hollow cylindrical section 17b starting from a flange section 17a and abutting on the inner circumference of the hub element 3. From the inner circumference near the flange section 17a there start two opposite flaps 17c, which abut on the outer circumference of the hollow needle 9 in the ready position in FIG. 10. When the needle 9 is removed from the catheter hub 2, the elastically deformed flaps 17c move inwards and close the valve. In this embodiment, an actuating element for opening the valve 17 is not necessary, because the pressure of the fluid from the syringe 14 displaces the flaps 17c radially outwards so that the liquid can flow out through the valve 17. In this embodiment of a check valve, a so-called duck-bill valve is concerned, whose construction is in itself known.

In FIG. 10, in order to allow the spring clip 13 to be held in the catheter hub during withdrawal of the hollow needle 9 from the catheter hub 2 until the radial projection 9b on the hollow needle engages with the rear wall 13c to cover the needle tip, in this embodiment there is formed on the inner circumference of the proximal hub element 5 a projection 5f which extends radially inwards and on which the radially outer areas of the spring arms 13a and 13b come to abut and hold the spring clip until the spring arms spring back radially inwards to cover the needle tip. The inner diameter of the projection 5f is designed only slightly smaller than the maximum radial dimension at the spring arms 13a and 13b, so that during assembly the spring clip 13 can be inserted by slight pressure into the position in the catheter hub as shown in FIG. 10.

In the embodiment of a catheter insertion device according to FIGS. 1 to 9, in the position of the valve actuating element 10 in FIG. 2 the valve disc 7 can be opened by low pressure produced by the syringe 4 for drawing off liquid from the catheter, wherein the elastic flaps 7b are bent upward by the low pressure. In the embodiment of FIG. 10, a drawing-off of liquid from the catheter is not possible, because the duck-bill valve does not open when there is low pressure on the proximal side.

It is convenient to fabricate the check valve in the form of a valve disc 7 or of the flap valve 17 from elastic silicon, while a correspondingly rigid plastic material is used for the hub elements 3 and 5 and for the valve actuating element 10.

What is claimed is:
1. A catheter insertion device comprising:
   a catheter hub comprising an interior cavity, an opening at a proximal end, and a catheter tube attached thereto and extending from a distal end;

a needle having a needle shaft defining a needle axis projecting distally of an end of a needle hub, said needle projecting through the catheter tube and comprising a needle tip;

a valve sized and shaped to obstruct fluid flow comprising a wall surface comprising a slit positioned inside the interior cavity of the catheter hub and in contact with the interior cavity; said valve remaining inside the interior cavity when the needle is removed from the catheter tube and the catheter hub and abuts a shoulder formed in the interior cavity of the catheter hub;

a valve actuating element slidingly disposed in the catheter hub to actuate the valve, the valve actuating element comprising a nose section having a tapered end for pushing the valve to open the slit of the valve and a plunger end having at least two plunger elements extending proximally of the nose section and having a gap therebetween to permit fluid flow to flow therethrough; the two plunger elements being sufficiently rigid to transfer a distally directed force to the nose section to push the valve to open the slit;

a needle protective device spaced from the needle tip in a ready position and movable relative to the needle tip to a protective position, at least in part, distally of the needle tip to prevent unintended needle sticks.

2. The catheter insertion device of claim 1, wherein the valve comprises three slits that converge at a single point.

3. The catheter insertion device of claim 1, wherein the catheter hub is made from two hub housing sections.

4. The catheter insertion device of claim 1, wherein the needle protective device is located between the two plunger elements of the valve actuating element in the ready position.

5. The catheter insertion device of claim 1, wherein the needle protective device comprises a proximal wall and two arms that converge to a single point.

6. The catheter insertion device of claim 1, wherein the valve actuating element further comprises a projection located proximally of the tapered nose section and projects radially outwardly of the nose section and abutting a shoulder of the catheter hub.

7. The catheter insertion device of claim 6, wherein the projection is distal of the two plunger elements.

8. The catheter insertion device of claim 1, wherein the needle protective device comprises an arm that is located, at least in part, in the catheter hub.

9. A catheter insertion device comprising:
a first hub comprising an interior cavity having a shoulder, a perimeter defining an opening at a proximal end, and a catheter tube having a distal end opening extending distally of the first hub;

a needle having a needle shaft defining a needle axis projecting distally of an end of a second hub, said needle projecting through the catheter tube and comprising a needle tip;

a valve sized and shaped to obstruct fluid flow comprising a plurality of slits positioned inside the interior cavity of the first hub and having a distal surface pushed against a shoulder in the interior cavity; said valve remaining inside the interior cavity when the needle is removed from the catheter tube and the first hub;

a valve actuating element slidingly disposed in the first hub to actuate the valve, the valve actuating element comprising a nose section having a tapered end with an opening structured to push the valve to open the plurality of slits and at least two plunger elements extending proximally of the nose section and having a gap therebetween; wherein the at least two plunger elements with the gap therebetween are disposed distally of the proximal end of the first hub and are slidable distally when a male implement projects into the opening of the first hub to transfer a distally directed force to the nose section to push the valve to open the plurality of slits;

a needle protective device positioned proximal of the valve and at least in part around the needle and distal of the proximal end of the second hub in a ready position, the needle protective device movable to prevent unintended needle sticks in a protective position.

10. The catheter insertion device of claim 9, wherein the valve has a radial outer perimeter abutting the interior cavity of the first hub.

11. The catheter insertion device of claim 9, wherein the valve comprises three slits that converge at a single point.

12. The catheter insertion device of claim 9, wherein the first hub is made from two hub housing sections.

13. The catheter insertion device of claim 9, wherein the needle protective device is located between the two plunger elements of the valve actuating element in the ready position.

14. The catheter insertion device of claim 9, wherein the valve actuating element further comprises a projection located proximally of the tapered nose section and projects radially outwardly of the nose section and abutting a shoulder of the first hub.

15. The catheter insertion device of claim 14, wherein the projection is distal of the two plunger elements.

16. The catheter insertion device of claim 9, wherein the needle protective device comprises an arm that is located, at least in part, in the first hub.

17. A catheter insertion device comprising:
a catheter hub comprising an interior cavity comprising a shoulder, an opening at a proximal end, and a catheter tube attached thereto and extending from a distal end;

a needle having a needle shaft defining a needle axis projecting distally of an end of a needle hub, said needle projecting through the catheter tube and comprising a needle tip;

a valve having a generally round outer contour sized and shaped to obstruct fluid flow positioned inside the interior cavity of the catheter hub; said valve remaining inside the interior cavity of the catheter hub when the needle is removed from the catheter tube and the catheter hub;

a valve actuating element slidingly disposed in the catheter hub for actuating the valve, the valve actuating element comprising a nose section having a tapered end being sufficiently rigid to open the valve, a projection on the valve actuating element located proximally of the tapered nose section abutting the shoulder of the catheter hub, and a plunger end extending proximally of the nose section having one or more gaps to permit fluid flow to flow therebetween and to transfer a distally directed force to the nose section to open the valve;

a needle protective device positioned, at least in part, around the needle between the valve and the proximal end of the needle hub in a ready position, the needle protective device being moveable to prevent unintended needle sticks in a protective position.

18. The catheter insertion device of claim 17, wherein the plunger end comprises at least two plunger elements defining the at least one or more gaps.

19. The catheter insertion device of claim 17, wherein the valve comprises three slits that converge at a single point.

20. The catheter insertion device of claim 17, wherein the catheter hub is made from two hub housing sections.

21. The catheter insertion device of claim 17, wherein the needle protective device located at the plunger end of the valve actuating element in the ready position.

22. The catheter insertion device of claim 17, wherein the needle protective device is spaced from the needle tip in the ready position and movable relative to the needle tip to the protective position, at least in part, distally of the needle tip to prevent unintended needle sticks.

23. The catheter insertion device of claim 17, wherein the projection is distal of the plunger end.

24. A catheter insertion device comprising:
 a catheter hub comprising an interior cavity comprising a shoulder, an opening at a proximal end, and a catheter tube attached thereto and extending from a distal end;
 a needle having a needle shaft defining a needle axis projecting distally of an end of a needle hub, said needle projecting through the catheter tube and comprising a needle tip;
 a valve comprising one or more slits movable to obstruct fluid flow positioned inside the interior cavity of the catheter hub; said valve remaining inside the interior cavity of the catheter hub when the needle is removed from the catheter tube and the catheter hub;
 a valve actuating element slidingly disposed in the catheter hub for opening the one or more slits and actuating the valve, the valve actuating element comprising a nose section having a tapered end made of a sufficiently rigid material to open the valve and a plunger end extending proximally of the nose section having at least one gap to permit fluid flow to flow thereacross and to transfer a distally directed force to the nose section to open the valve, said plunger end being provided at the opening of the catheter hub for pushing by a medical implement;
 a needle protective device positioned, at least in part, around the needle between the valve and the proximal end of the needle hub in a ready position, the needle protective device being moveable to prevent unintended needle sticks in a protective position.

25. The catheter insertion device of claim 24, further comprising a luer tip positioned inside the opening at the proximal end of the catheter hub after the needle protective device is in the protective position.

26. The catheter insertion device of claim 25, wherein the luer tip abuts a proximal end of the plunger end of the valve actuating element and the at least one gap is located therebetween.

27. The catheter insertion device of claim 24, further comprising a fluid path between a distal most end of the valve actuating element and a proximal most end of the valve actuating element.

28. The catheter insertion device of claim 27, further comprising a second gap at the plunger end.

29. The catheter insertion device of claim 28, further comprising a projection that extends radially outwardly of the valve actuating element for abutting a shoulder in the catheter hub.

* * * * *

UNITED STATES PATENT AND TRADEMARK OFFICE
CERTIFICATE OF CORRECTION

PATENT NO. : 8,540,728 B2
APPLICATION NO. : 13/630251
DATED : September 24, 2013
INVENTOR(S) : Woehr et al.

It is certified that error appears in the above-identified patent and that said Letters Patent is hereby corrected as shown below:

On the Title Page

On page 1, column 1, Item (57) in the abstract, delete "attached:" and insert -- attached; --, therefor.

On page 3, column 2, Item (56) line 17, delete "for" and insert -- and --, therefor.

On page 3, column 2, Item (56) line 19, delete "Standar," and insert -- Standard, --, therefor.

In the Specification

In column 1, line 66, delete "front" and insert -- proximal and distal --, therefor.

In column 3, line 6, delete "lob" and insert -- 10b --, therefor.

In column 4, line 1, delete "Sc" and insert -- 5c --, therefor.

Signed and Sealed this
Twenty-first Day of October, 2014

Michelle K. Lee
*Deputy Director of the United States Patent and Trademark Office*